United States Patent [19]

Kula et al.

[11] Patent Number: 4,877,734
[45] Date of Patent: Oct. 31, 1989

[54] MICROBIOLOGICALLY PRODUCED α-ACETYLAMINO CINNAMIC ACID ACYLASE, METHOD OF ITS PRODUCTION AND ITS USE

[75] Inventors: Maria-Regina Kula, Niederziehr-Hambach; Werner Hummel, Titz; Horst Schütte, Salzgitter; Wolfgang Leuchtenberger, Bruchkobel, all of Fed. Rep. of Germany

[73] Assignee: Degussa Aktiengesellschaft and Gesellschaft für biotechnologische Forschung-mit beschränkter Haftung GBF, Frankfurt am Main, Fed. Rep. of Germany

[21] Appl. No.: 66,492

[22] Filed: Jun. 26, 1987

[30] Foreign Application Priority Data

Jun. 28, 1986 [DE] Fed. Rep. of Germany ....... 3621839

[51] Int. Cl.$^4$ .......................... C12N 9/80; C12N 9/78; C12N 9/02; C12P 13/22
[52] U.S. Cl. ................................... 435/228; 435/227; 435/189; 435/108; 435/840
[58] Field of Search ............... 435/227, 108, 128, 840, 435/228, 189

[56] References Cited

U.S. PATENT DOCUMENTS

| | | | |
|---|---|---|---|
| 4,590,161 | 5/1986 | Kula et al. ......................... | 435/108 |
| 4,743,547 | 5/1988 | Kitamura et al. .................. | 435/108 |
| 4,755,466 | 7/1988 | Yokozeki et al. .................. | 435/108 |

OTHER PUBLICATIONS

Hummel, W. et al., (1987) Appl. Microbiol. Biotechnol 27, 283–291.

*Primary Examiner*—Elizabeth C. Weimar
*Assistant Examiner*—Charles L. Patterson
*Attorney, Agent, or Firm*—Cushman, Darby & Cushman

[57] ABSTRACT

A microbiologically produced α-acetylamino cinnamic acid acylase and a method for its production from Brevibacterium species NCIB 12246 or NCIB 12247. The new enzyme can be used as constituent of a coupled enzyme system for enzymatic conversions which run via the intermediary stage α-imino-β-phenylpropionic acid or phenylpyruvic acid.

5 Claims, No Drawings

MICROBIOLOGICALLY PRODUCED α-ACETYLAMINO CINNAMIC ACID ACYLASE, METHOD OF ITS PRODUCTION AND ITS USE

The invention relates to a previously un-described enzyme which catalyzes reactions of the following type:

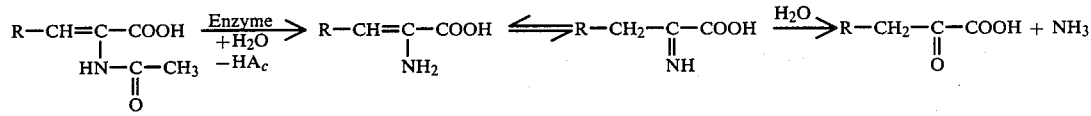

A particularly good reaction is obtained with $R=C_6H_5-$. The enzyme α-acetylamino cinnamic acid acylase, is characterized by the following properties:

(1) Reactivity:
It reacts with α-acetylamino cinnamic acid with formation of α-imino-β-phenylpropionic acid or phenylpyruvic acid respectively;

(2) Substrate specificity:
It hydrolyzes α-acetylamino cinnamic acid (referred to below as "ACA"), but not other α-acetylamino carboxylic acids such as acetylamino acrylic acid or N-acetylphenylalanine;

(3) Optimum pH:
The optimum pH is 7.5 ±1;

(4) pH stability:
It exhibits a good stability in a pH range between 6.9 and 9.4 (more than 90% residual activity after 2 weeks at 4° C.);

(5) Optimum temperature:
The optimum temperature is 52° C. at a pH of 7.5;

(6) Temperature resistance:
At 55° C., 80% residual activity can still be demonstrated after a 30-minute incubation;

(7) Influences of inhibitors and activators:
In particular, compounds (p-mercuric benzoate and $Hg_2Cl_2$), $CdCl_2$ and o-phenanthroline have an inhibiting action and the addition of dithiothreitol (1 mmole) activates the enzyme;

(8) Molecular weight:
The molecular weight is 50,000±5,000 Daltons;

(9) Subunits:
The molecule consists of 2 equally large subunits, each with 26,000±3,000 Daltons;

(10) The $K_M$ value for the substrate α-acetylamino cinnamic acid at pH 7.5 is 0.45 mmoles.

The α-acetylamino cinnamic acid acylase of the invention can be produced by means of two Brevibacterium strains which were deposited on Feb. 14, 1986 in the National Collection of Industrial Bacteria in Aberdeen (Scotland) under the numbers NCIB 12246 and NCIB 12247.

The following properties show that the two microorganisms belong to the genus Brevibacterium:

They grow in short gram-positive rods which turn with increasing age into coccoid forms. The cells are immobile and form no spores. Growth occurs strictly aerobically. No acid is formed from glucose. Catalase reaction and nitrate reduction are positive, urea splitting positive, decomposition of gelatine, casein and starch negative, $H_2S$ formation negative, growth at 41° C. negative. Arabinose, mannose and galactose were demonstrated as cell wall sugar. The microorganisms can be preserved as lyophilized culture by freezing at −80° C. or in liquid nitrogen at −196° C. Working cultures are kept on slant agar tubes (ACA medium).

In order to produce the α-acetylamino cinnamic acid acylase of the invention, Brevibacterium spec. NCIB 12246 or NCIB 12247 is aerobically cultured in an aqueous nutrient medium which contains a source for carbon and nitrogen, thiamine, mineral salts and α-acetylamino cinnamic acid as inductor at an initial pH between 6.0 and 8.0 and a temperature between 25° C. and 35° C., the cell mass is separated out and the enzyme isolated from the cells.

Larger amounts of the enzyme can be produced, for example, by culturing Brevibacterium spec. NCIB 12246 or NCIB 12247 in a known manner in a bioreactor on the desired scale, e.g., on a 10 liter scale. The following is important for a successful culture:

a good aeration (obligatorily aerobic organism);
an initial pH in the medium between 6.0 and 8.0;
the presence of mineral salts (e.g. in complex form as corn steep liquor);
the presence of slight amounts of thiamine (1 to 2 μg/l) and
the presence of ACA (0.2 to 0.4% by weight) in the medium for induction of the enzyme.

The isolation of the enzyme is possible after disruption of the cells by the combination of known methods of enzyme purification. It can be used as constituent of a coupled enzyme system for enzymatic conversions which run via the intermediary stage α-imino-β-phenylpropionic acid or phenylpyruvic acid. Thus, it can be combined, for example, with a suitable dehydrogenase in order to convert ACA into a corresponding α-amino carboxylic acid or α-hydroxycarboxylic acid. Combined with an L-phenylalanine dehydrogenase, it converts ACA, for example, into L-phenylalanine, combined with an L-2-hydroxy-4-methylpentanoic acid dehydrogenase into L-phenyl lactic acid and combined with a D-2-hydroxy-4-methylpentanoic acid dehydrogenase into D-phenyl lactic acid.

The invention is explained in more detail in the following examples. Percentages are given as percentages by weight, unless otherwise indicated.

Example 1

Screening for α-acetylamino cinnamic acid acylase producers 10 soil samples from the area of Braunschweig were suspended with sterile saline solution (0.9% NaCl), diluted in a customary manner and aliquots of the aqueous supernatant were put with a spatula on Petri dishes containing a solid substrate. The substrate had the following composition (ACA-medium):

| | | |
|---|---|---|
| α-acetylamino cinnamic acid (ACA) | 5 | g |
| $(NH_4)_2SO_4$ | 0.25 | g |
| $K_2HPO_4$ | 2 | g |
| yeast extract | 0.2 | g |
| trace element solution | 1 | ml |
| $MgSO_4 \cdot 7H_2O$ | 100 | mg |
| $CaCO_3$ | 20 | mg |
| distilled water | 1 | liter |

| | | |
|---|---|---|
| agar | 20 | g |
| pH value | 7.5 | |

The medium was sterilized by autoclaving and, after cooling, 1 ml sterilely filtered vitamin solution was added, per 1 liter of medium as well as 50 mg cycloheximide (actidione) per 1 liter (composition of the vitamin solution according to H. G. Schlegel, "Allgemeine Microbiologie" [General M.], Thieme Verlag, p. 169, 1981) and the substrate poured into sterile Petri dishes.

The inoculated plates were incubated 3 to 4 days at 27° C. After growth of the microorganisms, the colony specimen was transferred from agar plates with a suitable colony number (50-200) in a sterile manner onto a velvet stamp, then stamped onto 2 plates which contained different substrates in agar: One plate contained the ACA medium indicated above and the other a nutrient medium containing phenylalanine with the following composition (phenylalanine medium):

| | | |
|---|---|---|
| L-phenylalanine | 10 | g |
| $KH_2PO_4$ | 2 | g |
| yeast extract | 0.2 | g |
| agar | 20 | g |
| distilled water | 1 | l |

The pH was set at 7.2.

The plates were incubated again for 3 to 5 days at 27° C. A comparison of the colony specimens was able to identify those organisms which can grow both on the ACA medium as well as on the phenylalanine medium. They were sub-cultured and kept in the following ACA medium.

The isolated microorganisms were then checked in normal manner for purity (dilution smear, microscoping). Strains which appeared uniform were then cultivated in 100 ml liquid medium (500 ml Erlenmeyer flask with 2 baffles) at 27° C. on a rotary shaking machine at 120 rpms. The liquid medium had the following composition:

| | | |
|---|---|---|
| α-acetylamino cinnamic acid (ACA) | 3 | g |
| $(NH_4)_2SO_4$ | 0.25 | g |
| yeast extract | 1 | g |
| corn steep liquor (dry powder) | 5 | g |
| $K_2HPO_4$ | 2 | g |
| distilled water | 1 | liter |
| pH | 7.5 | |

After 2 to 3 days, the content of the shaking flask was centrifuged (20 minutes at 10,000 g in a refrigerated centrifuge) and the sedimentated cells were suspended in 0.05M potassium phosphate buffer (pH 7.4) (4 ml buffer per 1 g moist bacterial mass).

The microorganisms in this suspension must then be disintegrated in a customary manner (e.g. agitation with fine glass beads, ultrasonic treatment, French press). We treated the suspension with glass beads (0.1 to 2.0 mm $\phi$), using 2 g glass beads per 1 ml cell suspension, and then the mixture was agitated in a test tube for 10 minutes with a laboratory shaker (type Reax 1-D-R, firm Heidolph). It was possible to effectively disintegrate most of the isolates under these conditions. Insoluble cell constituents and the glass beads were separated out by centifugation (2 minutes with 12,000 rpms in an Eppendorf table centrifuge). The supernatant was then tested as an enzyme source (crude extract). A photometric test was used to assay the enzyme. The test batch contained:

| | |
|---|---|
| 0.7 M | ammonium chloride/ammonia buffer for pH 9.2 |
| 0.1 mM | NADH |
| 10 mM | ACA |
| 1 U/ml | L—phenylalanine-dehydrogenase and limiting amounts of acylase (1–20 μg protein per test) |

The decrease of the absorption of NADH at 340 nm was measured. A zero value was subtracted from the values obtained when the test was run without the addition of ACA. The enzyme activity is indicated in international units, one unit signifying the decrease of 1 μmole NADH/min.

The strains Brevibacterium spec. 37/3 (NCIB 12246) and 38/3 (NCIB 12247) displayed the highest activity in this test. The strain 37/3 was used for a production of the acylase on a larger scale.

Example 2:

Production of the α-acetylamino cinnamic acid acylase (a) Culture of Brevibacterium spec. 37/3 on a 10 liter scale A bioreactor was used which was filled with 10 liters of medium.

The medium contained, per liter:

| | |
|---|---|
| 3 | g ACA |
| 0.25 | g $(NH_4)_2SO_4$ |
| 1 | g yeast extract |
| 10 | g corn steep liquor (dry powder) |
| 2 | g $K_2HPO_4$ |

The pH was 7.5.

After sterilization, the medium was inoculated with 300 ml of a preculture which had been cultured 28 hours in the same medium. The growth conditions in the fermenter were:

| | |
|---|---|
| temperature | 30° C. |
| aeration rate | 60 liters air per hour |
| turbine agitator with 250 rpms | |

Samples (100 ml) were taken at various times of the growth and the maximum obtainable enzyme content and the most favorable harvesting time were determined after a test for enzymatic activity in these cells. In addition, the opacity (optical density) at 578 nm was measured to determine the growth of the culture. It was found that the main amount of acylase is formed when the organism has reached the stationary growth phase. After a maximum value has been reached, the enzyme activity drops again relatively rapidly.

(b) Recovery of the crude extract

The moist bacterial mass (230 g) was suspended in 20 mM phosphate buffer (pH 7.5) with the addition of 0.1% (v/v) 2-mercaptoethanol, so that the concentration of the cell suspension was 40% (final volume 575 ml). The cell components were stabilized from the refrigerated suspension (~4° C.) by a mechanical cell disintegration in a glass-bead mill of the Bachofen company (Dyno-Mill, type KDL). The 300 ml grinding container was filled with 0.25–0.5 mm glass beads, so that a bulk volume of 255 ml resulted (85%). The disruption was performed at an agitation or speed of 3,000 rpms and a flowthrough rate of 5 liters per hour. The refrigerating jacket of the grinding container as well as the agitation shaft bearing were refrigerated during running with ethylene glycol solution of −20° C. in order to prevent, to a great extent, a warming of the product. After 3 passes, a disintegration degree at 90% was achieved. The pH of the suspension was set after homogenization with potassium hydroxide at pH 7.5.

(c) Liquid-liquid partition

The cell fragments should be separated out of the crude extract with the first partition step according to the procedure described in Published German Specification DE PS 26 39 129. To this end, an aqueous two-phase system was produced which contained 10% (w/w) polyethylene glycol 6,000, 7% (w/w) phosphate buffer for pH 8.0, 0.05M sodium chloride and 575 ml crude extract in a 1.15 kg system. In order to achieve equilibrium of the distribution, the two-phase system was agitated for one hour and subsequently separated out by centrifugation.

The upper phase (745 ml) contained over 90% of the ACA acylase. The lower phase contained cell fragments as well as proteins extracted under these conditions into the lower phase and was discarded. The upper phase containing enzymes was compounded with 8% (w/v) phosphate buffer for pH 6.0 and 0.6M sodium chloride, calculated for a final volume of 1.5 liters, and agitated for 1 hour. The developing polyethylene glycol/salt system could be completely separated in a settler in approximately 1 hour. In this distribution step, the ACA acylase was extracted almost completely into the lower phase. The separation of the phases occurred by means of draining off the lower phase (1040 ml).

(d) Chromatography on phenyl Sepharose Cl–4B

The salt-rich lower phase, which contained the ACA acylase, was chromatographed directly using the hydrophobic phenyl Sepharose Cl–4B. The advantage of this method resides in the fact that a time-consuming dialysis of the salt-rich lower phase before the chromatography step is eliminated. The phenyl Sepharose Cl–4B had been equilibrated with a buffer which contained 50 mM phosphate buffer for pH 7.5, 0.1% (v/v) 2-mercaptoethanol and 1M ammonium sulfate (start buffer). The lower phase of the second partition step was applied to a 5×11 cm column and rewashed with two column volumes of start buffer. The ACA acylase was subsequently eluted with a 1 mM phosphate buffer for pH 7.5.

(e) Fast protein liquid chromatography (FPLC) on Mono Q

The eluate was applied over a super loop onto a 0.5×5 cm Mono Q column (FPLC system of the firm Pharmacia, Uppsala, Sweden) and chromatographed at a maximum pressure of 40 bars. 2 passages were necessary for the protein amount of 58 mg. The anion exchanger had been previously equilibrated against a 10 mM phosphate buffer for pH 7.5 (start buffer).

The ACA acylase was eluted with a linear 20 ml gradient which contained 0.1 to 0.4M sodium chloride in start buffer. The elution occurred from 0.25 to 0.3M sodium chloride. The time of such a chromatography is to be set at approximately 20 minutes.

(f) Fast protein liquid chromatography (FPLC) on Superose 12

The column (HR 10/30) filled with Superose 12 was equilibrated with a buffer which contained 50 mM phosphate buffer for pH 7.5 and 0.15M sodium chloride.

The eluate from the Mono Q column was first concentrated in a Minicon concentrator of the firm Amicon to a volume of 500 μl and then gel-filtrated in 2 passages of 250 μl on Superose 12. The time for a gel filtration on Superose 12 (HR 10/30-column; pressure ~30 bars) is approximately 40 minutes. The active fractions were combined, compounded with 50% (w/v) glycerol and stored at −20° C. The results of the purification are described in table 1.

TABLE 1

Purification of ACA-Acylase

| Purification step | Volume ml | Protein mg | Total Activity U | Specific Activity U/mg | Yield % | Enrichment factor |
|---|---|---|---|---|---|---|
| Crude extract | 575 | 1,944 | 500 | 0.26 | 100 | 1 |
| Upper Phase | 745 | 521 | 455 | 0.87 | 91 | 3.3 |
| Lower Phase | 1,040 | 416 | 415 | 1.0 | 83 | 3.8 |
| Phenyl-Sepharose Cl–4B | 197 | 58 | 345 | 5.9 | 69 | 23.1 |
| FPLC-Mono Q | 4.3 | 17 | 303 | 17.8 | 61 | 68.5 |
| FPLC-Superose S 12 | 3.6 | 8.4 | 240 | 28.6 | 48 | 110 |

Test with D-2-Hydroxy-4-methylpentanoic acid-dehydrogenase
Purification from 230 g bacterial wet mass Example 3

Induction of α-acetylamino cinnamic acid acylase (a) Changing of the culture medium The acylase is formed when the strain Brevibacterium spec. 37/3 is cultured in a medium with ACA as source for Carbon and Nitrogen. The enzyme yields (U/g ACA) are, however, relatively low. As table 2 shows, the yield can be increased if the medium contains suitable nitrogen containing compounds in addition. Carbon sources such as glycerol or glucose suppress the formation of acylase.

TABLE 2

Acylase activity as a function of the composition of the medium (all media contained 2 g/l $KH_2PO_4$, vitamins + trace elements; the pH was 7,5)

| medium g/l | U/l | mU/mg |
|---|---|---|
| ACA (5) | 33 | 60 |
| ACA (5) + $(NH_4)_2SO_4$ (0.25) | 80 | 90 |
| ACA (5) + yeast extract (1) | 40 | 70 |
| ACA (5) + corn steep liquor (5) | 100 | 95 |
| ACA (5) + corn steep liquor (5) + $(NH_4)_2SO_4$ (0.25) | 110 | 95 |
| ACA (5) + glycerol (10) | 0 | 0 |
| ACA (5) + glucose (10) | 0 | 0 |

(b) Changing of the ACA concentration

Different concentrations of ACA were added to a base medium of

| | |
|---|---|
| 5 | g corn steep liquor |
| 0.25 | g $(NH_4)_2SO_4$ |
| 2 | g $KH_2PO_4$ |
| 1 | ml vitamin solution |
| 1 | ml trace element solution |
| 1 | liter $H_2O$ |

Table 3 shows that a good activity is obtained in the crude extract if the medium contains 2 to 5 g ACA per l.

TABLE 3

Enzyme content during culturing in the presence of increasing amounts of ACA

| α-acetylamino cinnamic acid (g/l) | acylase U/l | U/mg |
|---|---|---|
| without ACA | 0 | 0 |
| 0.5 | 39 | 0.036 |
| 1 | 51 | 0.068 |
| 2 | 95 | 0.100 |
| 3 | 112 | 0.108 |
| 4 | 136 | 0.116 |
| 5 | 169 | 0.105 |

Example 4

Dependency of the reaction speed on the pH

The reaction speed of the hydrolytic splitting of acetic acid from the compound α-acetylamino cinnamic acid in the presence of ACA acylase, and of the subsequent reductive amination of the produced phenyl pyruvate in the presence of L-phenylalanine dehydrogenase to L-phenylalanine, or of the hydrogenation of the produced phenyl pyruvate in the presence of D-2-hydroxy-4-methylpentanoic acid dehydrogenase to D-phenyl lactic acid, was investigated as a function of the pH of the reaction solution.

Test batches had the following composition in combination with the L-phenylalanine dehydrogenase:

| 0.23 | mM NADH |
| 16 | mM ACA |
| 0.5 | U L—phenylalanine dehydrogenase |
| 0.7 | M ammonium chloride solution | at different pH values and limiting amounts of ACA acylase.

Selected pH values were set, between pH 7.5 and 10.3, by the addition of ammonia or hydrochloric acid to the 0.7M ammonium chloride solution, before the test batches were mixed together.

The optimum reaction speed is in a pH range between 7.5 and 9.

Test batches had the following composition in combination with the D-2-hydroxy-4-methylpentanoic acid dehydrogenase:

| 0.18 | mM NADH |
| 0.88 | mM ACA |
| 2.7 | U D-2-hydroxy-4-methylpentanoic acid dehydrogenase |
| 0.1 | M phosphate buffer at different pH's and limiting amounts of ACA acylase. |

The selected pH values were between pH 6.2 and 8.0. The optimum reaction speed is in a pH range between 6.5 and 7.8.

Example 5

Optimum temperature

The temperature dependency of the hydrolytic splitting of acetic acid from the compound α-acetylamino cinnamic acid was investigated in the presence of ACA acylase and of D-2-hydroxy-4-methylpentanoic acid dehydrogenase.

The test batch for the hydrogenation of the phenyl pyruvate had the following composition:

| 0.23 | mM NADH |
| 5 | mM ACA |
| 0.1 | M phosphate buffer for pH 7.5 |

This reagent mixture was incubated for 10 minutes at different temperatures between 25° C. and 60° C., compounded each time with 2.5 U D-2-hydroxy-4-methylpentanoic acid dehydrogenase as well as limiting amounts of ACA acylase and then the speed of the reaction was measured at the selected incubation temperature in a spectral photometer. The maximum reaction speed was reached at 52° C. at which it was 2.5 times higher than at the standard temperature of 30° C.

Example 6 pH stability of ACA acylase

The pH stability of ACA acylase was investigated at pH's in the range of 5.0 to 11.0. The enzyme was maintained for defined times at different pH's and thereafter the ACA acylase activity was determined under standard conditions at 30° C. The enzyme was diluted experimentally 1:11 with 100 mM of buffers which exhibited different pH's. The following buffers were used for these different pH ranges:

| 100 mM | citric acid/NaOH | pH 5.0; 5.5; 6.0; |
| | potassium phosphate | pH 6.0; 6.5; 7.0; 7.5; 8.0; |
| | tris/HCl | pH 8.0; 8.5; 9.0; |
| | NH$_4$Cl/NH$_4$OH | pH 9.0; 9.5; |
| | glycine/NaCl/NaOH | pH 10.0; 10.5; 11.0; 11.5 |

Standard conditions:

| 0.23 | mM NADH |
| 5 | mM ACA |
| 0.1 | M phosphate buffer for pH 7.5 |
| 2.5 | U D-2-hydroxy-4-methylpentanioc acid dehydrogenase limiting amounts of ACA acylase. |

The following Table 4 shows the residual activity of ACA acylase in percent after 1 hour, 1 day, 1 week and 2 weeks.

After 2 weeks, over 90% of the original ACA acylase activity could still be demonstrated in a pH range of 6.9 to 9.4.

TABLE 4 pH Stability of the ACA-acylase

| Buffer 0.1 M | Measured pH Value | (%) residual activity After | | | |
|---|---|---|---|---|---|
| | | 1 hour | 1 day | 1 Week | 2 Weeks |
| Citric Acid/ | 4.95 | 26 | 2 | — | — |
| NaOH | 5.35 | 86 | 17 | 5 | — |
| | 5.85 | 99 | 69 | 20 | 11 |
| | 5.95 | 99 | 75 | 34 | 14 |
| Potassium | 6.45 | 99 | 99 | 96 | 54 |
| phosphate | 6.9 | 99 | 99 | 99 | 93 |
| | 7.4 | 99 | 99 | 99 | 90 |
| | 7.85 | 99 | 99 | 99 | 75 |
| | 7.9 | 99 | 99 | 98 | 93 |
| Tris/HCl | 8.0 | 99 | 99 | 94 | 94 |
| | 9.12 | 99 | 99 | 86 | 90 |
| NH$_4$Cl/NH$_4$OH | 8.95 | 99 | 99 | 79 | 93 |
| | 9.42 | 99 | 99 | 87 | 91 |
| | 10.0 | 99 | 99 | 90 | 80 |
| Glycin/ | 10.3 | 99 | 99 | 90 | 5 |
| NaCl/ | 10.7 | 93 | 52 | 18 | — |

TABLE 4-continued

| Buffer | pH Stability of the ACA-acylase | | | | |
|---|---|---|---|---|---|
| | Measured | (%) residual activity After | | | |
| 0.1 M | pH Value | 1 hour | 1 day | 1 Week | 2 Weeks |
| NaOH | 11.1 | 44 | 5 | — | — |

Example 7

Temperature stability of ACA acylase

The temperature stability of ACA acylase was investigated in a temperature range of 25° to 60° C. The enzyme was incubated for 10, 20 and 30 minutes at the selected temperature in phosphate buffer (pH 7.5). Subsequently, the remaining ACA acylase activity was determined under standard conditions at 30° C.

Standard conditions:

---

0.23 mM NADH
5 mM ACA
0.1 M phosphate buffer for pH 7.5
2.5 U D-2-hydroxy-4-methylpentanoic acid dehydrogenase
limiting amounts of ACA acylase.

---

After a 30-minute incubation at 55° C., 80% of the initial activity can still be demonstrated and as the incubation temperature increases fruther, the ACA acylase is rapidly denatured.

Example 8

Influences of inhibitors and activators

The influence of different inhibitors and activators on the activity of ACA acylase and the resulting reaction speed of the hydrolytic splitting of acetic acid from the compound α-acetylamino cinnamic acid was measured under standard conditions, as described in Example 7. (Deviation: The tests with bivalent metal ions were performed in 0.1M tris/HCl buffer for pH 8.0.)

The results are collected in table 5.

TABLE 5

| Influences of inhibitors and activators | | |
|---|---|---|
| Reagent | Concentration (nM) | Residual Activity (%) |
| without addition | 0 | 100 |
| o-phenanthroline | 1 | 72 |
| | 10 | 45 |
| 2,2-dipyridyl | 1 | 97 |
| | 10 | 69 |
| EDTA | 1 | 111 |
| | 10 | 102 |
| p-mercuric benzoate | 1 | 41 |
| | 10 | 3 |
| dithiothreitol | 1 | 146 |
| | 10 | 123 |
| 2-mercaptoethanol | 1 | 100 |
| | 10 | 100 |
| red. glutathione | 1 | 102 |
| | 10 | 81 |
| $MgCl_2$ | 1 | 100 |
| | 10 | 100 |
| $MnCl_2$ | 1 | 63 |
| $CaCl_2$ | 1 | 99 |
| | 10 | 99 |
| $CdCl_2$ | 1 | 72 |
| | 10 | 29 |
| $HgCl_2$ | 1 | 51 |
| | 10 | 0 |
| $NiCl_2$ | 1 | 83 |
| | 10 | 53 |
| $ZnCl_2$ | 1 | 86 |

TABLE 5-continued

| Influences of inhibitors and activators | | |
|---|---|---|
| Reagent | Concentration (nM) | Residual Activity (%) |
| | 10 | 34 |

Example 9

Determination of the molecular weight of ACA acylase and of the subunits

The molecular weight of the native enzyme was established by gel filtration on superose 12. The column (1.0×30 cm) coupled to an FPLC system (The firm Pharmacia, Uppsala, Sweden) was operated at a flow-through rate of 0.4 ml/min, whereby 75 μl of the enzyme purified with mono Q served as test material.

Cytochrome C, pepsin, ovalbumin, bovine serum albumin (BSA), D-2-hydroxyisocaproate dehydrogenase, L-2-hydroxyisocaproate dehydrogenase, aldolase, L-alanine dehydrogenase and L-Leucine dehydrogenase from B. cereus and ferritin were used as calibration proteins.

The molecular weight of ACA acylase is 50,000±5,000 Daltons.

The size and the number of the subunits of the enzyme could be determined by gel electrophoresis in the presence of sodium dodecylsulate (SDS). The molecular weight of the subunits is 26,000±3,000 Daltons. That means that ACA acylase consists of 2 identical subunits Hemoglobin, β-lactoglobulin, chymotrypsinogen A, pepsin, ovalbumin and BSA were used for the calibration curve.

Example 10

Dependency of the ACA acylase activity on the substrate concentration (a) The dependency of the reaction speed of the hydrolytic splitting of acetic acid from the compound α-acetylamino cinnamic acid in the presence of ACA acylase and subsequent reductive amination in the presence of L-phenylalanine dehydrogenase to L-phenylalanine was investigated in the following test batch:

---

0.7 mM ammonium chloride/ammonia buffer (pH 8.5)
0.23 mM NADH
0.5 U L—phenylalanine dehydrogenase
limiting amounts of ACA acylase.

---

The α-acetylamino cinnamic acid concentration was varied within a range of 1–36 mM. It was found that the optimum reaction speed is achieved at 16 mM. The $K_M$ value for α-acetylamino cinnamic acid is 3.9 mM.

(b) the dependency of the reaction speed in the hydrolytic splitting of acetic acid from the compound α-acetylamino cinnamic acid in the presence of ACA acylase and subsequent hydrogenation of phenyl pyruvate in the presence of D-2-hydroxy-4-methylpentanoic acid dehydrogenase to D-phenyl lactic acid was investigated in the following test batch:

---

0.1 M phosphate buffer (pH 7.5)
0.23 mM NADH
0.8 U D—2-hydroxy-4-methylpentanoic acid dehydrogenase -continued limiting amounts of ACA acylase.

The α-acetylamino cinnamic acid concentration was varied within a range of 0.1–18 mM. It was found that the optimum reaction speed is achieved at 5 mM. The $K_M$ value for α-acetylamino cinnamic acid is at 0.45 mM.

The measurements show that the $K_M$ value is a function of the pH:

At pH 7.5 it is 0.45 mM, at pH 8.5 it is at 3.9 mM. The value for characterizing the enzyme should be the value which was determined at the optimum pH, i.e., the $K_M$ value for the substrate ACA is at 0.45 mM (pH 7.5).

Example 11

Substrate specificity of ACA acylase

In a series of parallel batches, the substrate α-acetylamino cinnamic acid was replaced by other compounds and tested to see to what extent the enzyme accepts other substrates. The following test batches were used depending on the substrate used:

1. Test with α-acetylamino cinnamic acid as substrate:

```
0.7 M NH4Cl
0.1 mM NADH
50 mM α-acetylamino cinnamic acid
1 U/ml L—phenylalanine dehydrogenase 0.1 U/ml ACA acylase
pH 9.2
```

The activity was measured (at 340 nm) by a photometric test as described in Example 1.

2. Test with α-acetylamino acrylic acid:

```
0.7 M NH4Cl
0.1 mM NADH
50 mM α-acetyl amino acrylic acid
1 U/ml L—alanine dehydrogenase
0.1 U/ml ACA acylase
pH 8.0
```

The activity was measured in an analogous manner (by a photometric test at 340 nm) (1 μmole NADH decrease would correspond to 1 μmole formation of alanine).

3. Test with peptides:

Other substrates used were N-acetyl-L-phenylalanine, N-methoxycarbonyl-D,L-phenylalanine and various peptides. The peptides used are listed in table 6. The test batch contained in these instances:

```
0.1 M potassium phosphate buffer (pH 7.5)
0.1 U/ml ACA acylase (17.8 U/mg)
50 mM substrate
```

The batches (1 ml altogether) were agitated (30° C.) and samples were taken at different times. The amino acids produced by the acylase action were quantitatively detected with the aid of an amino acid analyzer. The activity of the enzymes is also indicated in this instance in international units-an activity of 1 U corresponds to the formation of 1 μmole amino acid per minute. The activities measured with the 3 test batches are listed in column 2 of Table 6 in mU/ml. For the determination of the relative activity (column 3 of Table 6), the activity of the α-acetylamino cinnamic acid as substrate was set equal to 100%.

TABLE 6

Substrate specificity of ACA acylase

| Substrate | Activity (mU.ml$^{-1}$) | Relative Activity (%) |
| --- | --- | --- |
| Amino acid derivatives: | | |
| α-acetylamino cinnamic acid | 125 | 100 |
| α-acetylamino acrylic acid | 0 | 0 |
| N—acetyl-L—phenylalanine | 0 | 0 |
| N—methoxycarbonyl-D,L—phenylalanine | 0 | 0 |
| peptides: | | |
| gly-L—phe | 40 | 32 |
| gly-D-phe | 0 | 0 |
| gly-gly-L—phe | 0 | 0 |
| L—ala-L—phe | 105 | 84 |
| L—leu-L—phe | 102 | 82 |
| L—phe-L—phe | 41 | 33 |
| L—his-L—phe | 44 | 35 |
| L—ser-L—phe | 36 | 29 |
| L—asp-L—phe | 38 | 30 |
| L—leu-L—tyr | 109 | 87 |
| L—leu-L—trp | 67 | 54 |
| L—ala-L—trp | 66 | 53 |
| L—ala-L—tyr | 78 | 62 |
| L—ala-L—his | 43 | 34 |

Example 12

Production of L-phenylalanine

If the ACA acylase is coupled with L-phenylalaninedehydrogenase, the intermediary product produced can be stereospecifically converted to L-phenylalanine by reductive amination. In order to regenerate the co-enzyme oxidized in the dehydrogenation reaction, formate dehydrogenase (E.C.1.2.1.2) and formate are added to the batch. $CO_2$ is then obtained as additional product. Different batches were incubated with different concentrations of ACA, which batches specifically contained:

```
400 mM ammonium formate (pH 9.2)
200 mM tris/HCl (pH 9.2)
0.3 mM NADH
  1 U/ml formate dehydrogenase (preparation
    according to Kroner et al.
    (1982) J. Chem. Technol. Bio-
    technol. 32, pp. 130–137)
    1U/ml L—phenylalanine dehydrogenase
    (preparation with 44 U/mg)
0.5 U/ml ACA acylase
20–300 mM ACA
```

The total volume was 1 ml, the incubation occurred under agitation at 28° C. The product formation was followed on an amino acid analyzer.

Table 7 shows that there was a practically complete conversion of the substrate to phenylalanine in all batches.

TABLE 7

Conversion of different amounts of ACA to L—phenylalanine

| Batch No. | α-acetylamino cinnamic acid (mM) | reaction time (hrs) | L—phenyl-alanine (mM) |
| --- | --- | --- | --- |
| 1 | 20 | 4 | 21 |
| 2 | 50 | 6.5 | 56 |
| 3 | 100 | 6.5 | 98 |
| 4 | 200 | 30 | 204 |

TABLE 7-continued

Conversion of different amounts of ACA to L—phenylalanine

| Batch No. | α-acetylamino cinnamic acid (mM) | reaction time (hrs) | L—phenyl-alanine (mM) |
|---|---|---|---|
| 5 | 300 | 75 | 306 |

The optical purity of the L-phenylalanine formed was checked in batch 5 with 300 mM substrate after 75 hours reaction. In this batch a part of the product was present in insoluble form as a crystal suspension (solubility of Phe in H$_2$O at 25° C.=180 mM). In order to bring the entire product into solution, 3 ml H$_2$O were added to the batch. The proteins were removed by gel filtration on Sephadex G-25 (Pharmacia) and the fraction with the low-molecular substances were taken up after freeze-drying with 4.5 ml H$_2$O.

A test on an amino acid analyzer yielded an L-phenylalanine content of 37.4 mM. A test with L-amino acid oxidase yielded 37 mM L-Phe. A test with D-amino acid oxidase was negative, and the detection limit is at 0.04 mM D-Phe. Example 13: Production of D-phenyl lactic acid (continuous)

ACA can be enzymatically converted to D-phenyl lactic acid by coupling the ACA acylase with a D-2-hydroxy acid dehydrogenase. The dehydrogenase used can be a corresponding D-lactate dehydrogenase (e.g. from Lactobacillus confusus, cf. W. Hummel et al., Eur. J. Appl. Microbiol. Biotechnol. 18:75–85, 1983) or a D-2-hydroxy-4-methylpentanoic acid dehydrogenase. The coenzyme regeneration is achieved in this example in the presence of formate with a formate dehydrogenase.

The batch (10 ml total volume) specifically contained:

```
400 mM sodium formate (pH 7.5)
200 mM tris/HCl (pH 7.5)
0.3 mM PEG (20,000)-NADH
  1 U/ml formate dehydrogenase
  1 U/ml D-2-hydroxy-4-methylpentanoic acid
    dehydrogenase (preparation with 270 U/mg)
0.5 U/ml ACA acylase (preparation with 6 U/mg)
 20 mM ACA
```

A continuous conversion is achieved in an enzyme membrane reactor. To this end, the reaction batch is pumped via an ultrafiltration membrane (type YM5, from the firm Amicon, exclusion limit 5,000 Daltons). Low-molecular constituents can be continuously removed from the reaction mixture thereby residence time 3 hours). The volume of the ultrafiltered product solution was continuously replaced in the test arrangement by substrate solution. The substrate solution contained:

```
400 mM sodium formate (pH 7.5)
200 mM tris/HCl (pH 7.5)
 20 mM ACA
```

The degree of conversion was determined by measuring the optical rotation α of the product solution polarimetrically. The product concentration can then be determined from a calibration curve set up with commercial D-phenyl lactic acid (Sigma).

Table 8 shows that ACA can be converted practically completely to D-phenyl lactic acid.

TABLE 8

Conversion of ACA (20 mM) to D-phenyl lactic acid

| Time (hours) | optical rotation (degrees) | product concentration mM | Conversion % |
|---|---|---|---|
| 5 | 202 | 12.1 | 61 |
| 10 | 305 | 18.1 | 91 |
| 15 | 330 | 20 | 100 |
| 20 | 330 | 20 | 100 |
| 25 | 330 | 20 | 100 |

What is claimed is:

1. A microbiologically produced α-acetylamino cinnamic acid acylase having the following properties:
   (i) reactivity:
      said acylase reacts with α-acetylamino cinnamic acid with the formation of α-imino-β-phenylpropionic acid or phenylpyruvic acid;
   (ii) substrate specificity:
      said acylase hydrolyzes α-acetylamino cinnamic acid but not acetylamino acrylic acid nor N-acetylphenylalanine;
   (iii) optimum pH:
      said acylase has a pH optimum of 7.5±1;
   (iv) pH stability:
      said acylase is stable between pH 6.9 and pH 9.4;
   (v) optimum temperature:
      said acylase has a temperature optimum of 52° C. at a pH of 7.5;
   (vi) temperature resistance:
      said acylase retains 80% of its activity after a 30-minute incubation at 55° C.;
   (vii) influences of inhibitors and activators:
      mercury compounds, CdCl$_2$ and o-phenanthroline exhibit an inhibitory effect on said acylase, and dithiothreitol activates said acylase;
   (viii) molecular weight;
      said acylase has a molecular weight of 50,000±5,000 Daltons;
   (ix) subunits:
      said acylase consists of 2 subunits each having a molecular weight of 26,000±3,000 Daltons; and
   (x) K$_M$ value:
      said acylase has a K$_M$ for α-acetylamino cinnamic acid of 0.45 mmoles at pH 7.5.

2. A method of producing the α-acetylamino cinnamic acid acylase of claim 1 which comprises:
   (i) aerobically culturing, at an initial pH between 6.0 and 8.0 and at a temperature between 25° C. and 35° C., Brevibacterium spec. NC1B 12246 or NC1B 12247 in an aqueous nutrient medium which contains a carbon source, a nitrogen source, thiamine, mineral salts and, as an inducer, α-acetylamino cinnamic acid, whereby a cell mass is formed;
   (ii) separating said cell mass from said nutrient medium; and
   (iii) isolating said acylase from said cell mass.

3. A microbiologically produced α-acetylamino cinnamic acid acylase produced by the method of claim 2.

4. A coupled enzyme system for enzymatic conversions which comprises:
   (i) the α-acetylamino cinnamic acid acylase according to claim 1, which acylase catalyzes the production of α-imino-β-phenylpropionic acid and phenylpyruvic acid from α-acetylamino cinnamic acid; and
   (ii) a second enzyme that catalyzes the further conversion of α-imino-β-phenylpropionic acid or phenylpyruvic acid.

5. The coupled enzyme system according to claim 4, wherein said second enzyme is a dehydrogenase.

* * * * *